United States Patent

Pirkle et al.

[11] Patent Number: 5,254,258
[45] Date of Patent: Oct. 19, 1993

[54] CHIRAL SELECTOR USEFUL FOR SEPARATION OF ENANTIOMERS OF β-AMINO ALCOHOL COMPOUNDS

[75] Inventors: William H. Pirkle, Champaign; John A. Burke, III, Urbana, both of Ill.

[73] Assignee: Research Corporation Technologies, Inc., Tucson, Ariz.

[21] Appl. No.: 761,212

[22] Filed: Sep. 17, 1991

[51] Int. Cl.$^5$ .............................................. B01D 61/38
[52] U.S. Cl. ................................. 210/643; 210/644; 210/658
[58] Field of Search ............ 210/650, 643, 644, 195.2, 210/658, 654, 638; 544/492, 158; 574/381, 365, 269, 419

[56] References Cited

U.S. PATENT DOCUMENTS 4,590,167  5/1986  Gunther et al. ............... 210/658 X
5,080,795  1/1992  Pirkle et al. ..................... 210/643

OTHER PUBLICATIONS

Pirkle, W. H., et al., "Chiral Stationary Phase Designed for β-Blockers," 557 *J. Chromatogr.*, 173-85 (Sep. 20, 1991).
Pirkle, W. H., et al., "Preparation of a Chiral Stationary Phase From an α-Amino Phosphonate," 1 *Chirality*, 57-62 (1989).

(List continued on next page.)

*Primary Examiner*—Frank Spear
*Attorney, Agent, or Firm*—Scully, Scott, Murphy & Presser

[57] ABSTRACT

Underivatized enantiomers of a β-amino alcohol compound are directly separated by means of a chiral selector compound having the formula

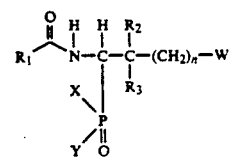

wherein

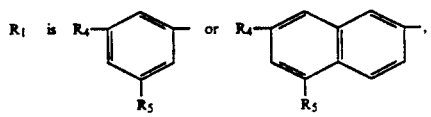

preferably $R_1$ is 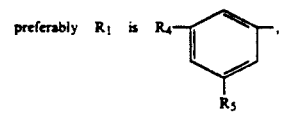

$R_2$ and $R_3$ are each independently lower alkyl, preferably methyl;
$R_4$ and $R_5$ are each independently $NO_2$, $N(R_6)_3^+$, $CN$, $COOR_2$, $SO_3H$ or $COR_8$, preferably $NO_2$;
$R_6$, $R_7$ and $R_8$ are each independently hydrogen or lower alkyl, preferably hydrogen or methyl,
W is H or $CH=CH_2$,
X and Y are each independently $OR_9$ or $NR_{10}R_{11}$, preferably X and Y are the same and most preferably X and Y are each $OR_9$, or X and Y together with the P to which they are attached form a 5- or 6-membered ring having the formula

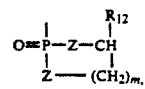

$R_9$, $R_{10}$, $R_{11}$ and $R_{12}$ are each independently hydrogen or lower alkyl, $R_9$ is preferably methyl, $R_{10}$, $R_{11}$ and $R_{12}$ are preferably hydrogen or methyl,
Z is O or NH,
n is 1 to 20, preferably 1 to 8 when W is H, and 1 to 3 when W is $CH=CH_2$, and
m is 1 or 2,
said compound being an R or an S enantiomer or a mixture of R and S enantiomers.

21 Claims, 5 Drawing Sheets

OTHER PUBLICATIONS

Pirkle, W. H., et al., "A Rational Approach to the Design of Highly Effective Chiral Stationary Phases for the Liquid Chromatographic Separation of Enantiomers," 2(2) J. Pharma. Biol. Anal., 173–181 (1984).

Patent Abstracts of Japan, 15: No. 445 (C-884) and JP,A,03190827 (Nippon Steel Corp.) Aug. 20, 1991.

Pirkle, et al., "A Widely Useful Chiral Stationary Phase for the High-Performance Liquid Chromatography Separation of Enantiomers", 103 J. Am. Chem. Soc., 3964–66 (1981).

Pettersson, et al., "Separation of Enantiomeric Amines by Ion-Pair Chromatography", 204 J. Chromatogr., 179–83 (1981).

Pirkle, et al., "A Rational Approach to the Design of Highly-Effective Chiral Stationary Phases", 316 J. Chromatogr., 585–604 (1984).

Wainer, et al., "The direct enantiomeric determination of (−)— and (+)—propranolol in human serum by high-performance liquid chromatography on a chiral statonary phase" 306 J. Chromatogr., 405–11 (1984).

Armstrong, et al., "Separation of Drug Steroisomers by the Formation of $\beta$-Cyclodextrin Inclusion Complexes", 232 Science, 1132–35 (1986).

Okamoto, et al., "Optical Resolution of $\beta$-Blockers by HPLC on Cellulose Triphenylcarbamate Derivatives", Chem. Lett., 1237–40 (1986).

Pirkle, et al., "Intermolecular $^1H[^1H]$ Nuclear Overhauser Effects in Diastereomeric Complexes: Support for a Chromatographically Derived Chiral Recognition Model", 108 J. Am. Chem. Soc., 5627–28 (1986).

Pettersson, et al., "Influence of Enantiomeric Purity of a Chiral Selector on Stereoselectivity", 407 J. Chromatogr., 217–29 (1987).

Pirkle, et al., "Reciprocity in Chiral Recognition Comparison of Several Chiral Stationary Phases", 404 J. Chromatogr., 107–15 (1987).

Pirkle, et al., "Systematic Studies of Chiral Recognition Mechanisms", 23–35 in Chiral Separations, Stevenson, et al., ed. (1988).

Aboul-Enein, et al., "Direct High-Performance Liquid Chromatographic Separation of Penbutolol Enantiomers on a Cellulose Tris-3,5-dimethylphenyl Carbamate Chiral Stationary Phase", 1 Chirality, 301–04 (1989).

Hermansson, "Enantiomeric separation of drugs and related compounds based on their interaction with $\alpha_1$-acid glycoprotein", 8 Anal. Chem., 251–59 (1989).

Moriguchi, et al., Abstract of Paper M/TU-P-017, "Liquid Chromatographic Separation of Enantiomers Upon Chiral Stationary Phases Comprised of (d)-N-(3-,5-Dinitrobenzoyl)-Penicillamine", The Thirteenth Symposium on Column Liquid Chromatography (1989).

Pirkle, et al., "Preparation of a Chiral Stationary Phase From an $\alpha$-Amino Phosphonate", 1 Chirality, 57–62 (1989).

Walhagen, et al., "Coupled-Column Chromatography on Immobilized Protein Phases for Direct Separation and Determination of Drug Enantiomers in Plasma", 473 J. Chromatogr., 371–79 (1989).

Erlandsson, et al., "Immobilized Cellulase (CBH I) as a Chiral Stationary Phase for Diret Resolution of Enantiomers", 112 J. Am. Chem. Soc., 4573–74 (1990).

Regis Chemical Company Catalog, Sec. 5, 42–54 (1990).

Pirkle et al. (1988) "An Improved Chiral Stationary Phase for the Facile Separation of Enantiomers", *Journal of Chromatography* vol. 144, No. 2, pp. 311–322.

$\alpha = 1.87$
$k'_1 = 3.29$

FIGURE 3b

$\alpha = 2.23$
$k'_1 = 3.43$

FIGURE 3c

$\alpha = 2.58$
$k'_1 = 4.33$

Bufuralol

CHIRAL SELECTOR USEFUL FOR SEPARATION OF ENANTIOMERS OF β-AMINO ALCOHOL COMPOUNDS

This invention was made with Government support under CHE-8714950 awarded by National Science Foundation. The Government has certain rights in the invention.

BACKGROUND OF THE INVENTION

1. Field of the Invention

This invention relates to the separation of enantiomers. This invention more particularly relates a chiral selector for separation of enantiomers. This invention especially relates to a chiral selector useful, for example, as a chiral stationary phase (CSP) in the liquid chromatographic (HPLC) separation of enantiomers of underivatized beta-amino alcohol compounds.

2. Description of the Prior Art

Stereoisomers are those molecules which differ from each other only in the way their atoms are oriented in space. Stereoisomers are generally classified as diastereomers or enantiomers; the latter embracing those which are mirror-images of each other, the former being those which are not. The particular arrangement of atoms that characterize a particular stereoisomer is known as its optical configuration, specified by known sequencing rules as, for example, either + or − (also D or L) and/or R or S.

Though differing only in orientation, the practical effects of stereoisomerism are important. For example, the biological and pharmaceutical activities of many compounds are strongly influenced by the particular configuration involved. Indeed, many compounds are only of widespread utility when provided in a given stereoisomeric form. Living organisms usually produce only one enantiomer of a pair. Only (−)-2-methyl-1-butanol is formed in yeast fermentation of starches; only (+)-lactic acid is formed in the contraction of muscle; fruit juices contain only (−)-malic acid and only (−)-quinine is obtained from a cincliona tree. In biological systems, stereochemical specificity is the rule rather than the exception, since the catalytic enzymes which are so important in such systems are optically active. The sugar (+)-glucose plays an important rule in animal metabolism and is the basic raw material in the fermentation industry; yet (−)-glucose is not metabolized by animals or fermented by yeasts. The mold *Penicillium glaucum* will only consume the (+)-enantiomer of an enantiomeric mixture of tartaric acid leaving (−)-tartaric acid intact. Only one stereoisomer of chloromycetin is an antibiotic. Not only does (+)-ephedrine not have any drug activity, but it interferes with the drug activity of its enantiomer. (−)-Carvone provides oil of spearmint with its distinctive odor while its enantiomer, (+)-carvone has the essence of caraway. Hence, it is desirable and often essential to separate stereoisomers to provide the useful version of an optically active chemical compound.

When diastereomers are involved, separation is generally not a significant problem because diastereomers have different physical properties, such as melting points, boiling points, solubilities in a given solvent, densities, refractive indices, etc. Hence, diastereomers may normally be separated from each other by conventional methods, such as fractional distillation, fractional crystallization, or chromatography.

Enantiomers, on the other hand, present a special problem because their physical properties are identical. They cannot as a rule —especially when in the form of a racemic mixture—be separated by ordinary methods: not by fractional distillation, because their boiling points are identical; not by conventional fractional crystallization, because (unless the solvent is optically active) their solubilities are identical; not by conventional chromatography because (unless the adsorbent is optically active) they are held equally onto the adsorbent. The problem of separating enantiomers is further exacerbated by the fact that conventional synthetic techniques almost always produce a mixture of enantiomers. When the mixture comprises equal amounts of enantiomers having different optical configurations, it is called a racemate or a racemic modification; and separation of the racemate into its respective enantiomers —this separation being generally known as a resolution— is, therefore, a process of considerable importance.

Various techniques for separating enantiomers are known. Most, however, are directed to small analytical quantities, meaning that, other drawbacks aside, when applied to preparative scale amounts (the milligram to kilogram range) a loss of resolution occurs. Hand separation —the oldest method of resolution— is not only impractical but can almost never be used since racemates seldom form mixtures of crystals recognizable as mirror-images.

Another method, known as an indirect separation, involves the conversion of a mixture of enantiomers —the racemate— into a mixture of diastereomers. The conversion is accomplished by reacting the enantiomers with an optically pure chiral derivatizing agent. The resultant diastereomers are separated from each other by talking advantage of their different physical properties. Once separated, by, for example, fractional crystallization, or more commonly, chromatography, the diastereomers are re-converted back into the corresponding enantiomers, which are now optically pure. Though achieving the requisite separation, the indirect method suffers in that it is time-consuming and can require large quantities of optically pure derivatizing agent which can be expensive and is oftentimes not recoverable. Moreover, the dederivatization step may itself result in racemization thus defeating the purpose of the separation earlier achieved.

A more current method which avoids some of the drawbacks attendant the indirect method is known as the direct method of separation. The direct method, much like the indirect method, involves the formation of a diasteromeric species. However, unlike the indirect method, this species is transient, with the stability of one species differing from the other.

In one application of the direct method, the mixture of enantiomers is allowed to interact with a chiral stationary phase (CSP), which, for example, could reside in a chromatographic column. The enantiomer that interacts more strongly with the chiral stationary phase than the other will have a longer residence time on the chiral stationary phase and hence a separation will occur. When the mode of interaction with the chiral stationary phase can be characterized, the elution order may be predicted. Examples of chiral stationary phases include those based on (L)-N-(3,5-dinitrobenzoyl)leucine, which is useful in separating enantiomers of N-aryl derivatized amino acids and esters and those based on (L)-N-[1-naphthyl)leucine which has been used to effectively separate N-(3,5-dinitrobenzoyl) derivatized amino compounds. HPLC columns packed with silica-bonded CSPs of a variety of pi-electron acceptors and pi-electron donors, including derivatives of phenylglycine, leucine, naphthylalinine and naphthylleucine are commercially available from Regis Chemical Company, Morton Grove, Ill.

In another application of the direct method, disclosed in copending and commonly assigned patent application Ser. No. 528,007, filed May 23, 1990, now U.S. Pat. No. 5,080,795, enantiomers of such compounds as amino acids, amino esters, sulfonides, alcohols, amines, sulfonic acids or derivatives thereof are separated by means of a liquid membrane containing a chiral carrier, such as derivatized amino acid, (S)-N-(1-naphthyl)leucine octadecyl ester. The chiral carrier is capable of forming a stable complex with one of the enantiomers. The liquid membrane is located on one side of a semi-permeable barrier, and the mixture of enantiomers is located on the other side of the liquid membrane. The liquid membrane containing the chiral carrier impregnates the semi-permeable barrier under conditions effective to permit or cause a stable complex between the chiral carrier and one of the enantiomers to form in the liquid membrane. The liquid membrane containing the stable complex is passed to a second location where the conditions are effective to dissociate the stable complex and the recovery of the complex-forming enantiomer. In one embodiment of this application, a hollow-fiber membrane is employed as the semi-permeable barrier.

It is widely recognized that stereoisomers of pharmaceutical agents may have drastically different pharmacological potencies or actions. For example, the so-called $\beta$-blockers, widely used in the treatment of angina pectoris and hypertension, differ considerably in the physiological responses they elicit. Typically, the (S) enantiomers are 50-500 fold more active than their antipodes and may differ also in the nature of the elicited responses. $\beta$-blockers are adrenergic blocking agents capable of blocking nerve impulses to special sites (beta acceptors) in the cerebellum in order to reduce the heartbeat rate and the force of heart contractions. Owing to their importance, many potential $\beta$-blockers have been developed and tested, and a number are now marketed. Known $\beta$-blockers include compounds identified as metoprolol, oxprenolol, propanolol, pindolol, pronethalol and bufuralol. The common aspect of the compounds is that they all have a $\beta$-amino alcohol structure.

In the present scientific climate, all stereo-isomers of a potential pharmaceutical must be evaluated individually. Consequently, methods of preparatively separating $\beta$-blocker stereoisomers and for ascertaining their stereochemical purity are of considerable current interest. Moreover, much effort continues to be expended by pharmacologists in the study of how $\beta$-blocker stereochemistry influences the extent and mode of their action. There are now a variety of liquid chromatographic methods which facilitate determinations of stereochemical purity of $\beta$-blockers, studies of differences in the rate of metabolism of their enantiomers and studies of the stereochemical pathways of metabolism. While it is possible and often practical to derivatize enantiomers with a chiral reagent so as to obtain diastereomers which are separable on an achiral column, there are potential disadvantages to this approach. In some instances, the enantiomers of $\beta$-blockers have been separated on achiral columns through the use of chiral mobile phase additives as reported by C. Petterson, et al. in *J. of Chromatogr.*, 204, 179-384 (1981) and 407, 217-229 (1987). However, the scope of this method remains undetermined, and it too is disadvantageous in some applications. Instances of derivatization with an achiral reagent prior to enantiomer separation on a column containing chiral stationary phases, CSPs, have been reported. However, the need for derivatization, and in the case of preparative separations—dederivatization, is an obstacle to be avoided if possible. The direct separation of underivatized enantiomers on a CSP is to be preferred but is neither always possible nor feasible.

The object of this invention is to provide a process for the separation of underivatized enantiomers of $\beta$-amino alcohol compounds, particularly $\beta$-blocker drugs.

Another object of this invention is to provide a process for the direct separation of underivatized enantiomers of $\beta$-amino alcohol compounds, particularly $\beta$-blocker drugs, by means of a chiral selector.

A further object of this invention is to provide a process for the direct separation of underivatized enantiomers of $\beta$-amino alcohol compounds, particularly $\beta$-blocker drugs, by means of liquid chromatography employing a chiral selector as a chiral stationary phase (CSP).

Yet another object of this invention is to provide a process for the direct separation of underivatized enantiomers of $\beta$-amino alcohol compounds, particularly $\beta$-blocker drugs, by means of a liquid membrane containing a chiral selector passing in contact with one side of a semi-permeable membrane while a mixture of the enantiomers are in contact with the other side of the semi-permeable membrane.

SUMMARY OF THE INVENTION

Briefly, the objects of this invention are achieved by employing a chiral selector having a particular formula so as to provide a series of three bonding sites compatible with corresponding sites on one of the enantiomers of the subject $\beta$-amino alcohol compound for which separation is desired.

The chiral selector of this invention is a chemical compound having the formula wherein $R_1$ is preferably $R_1$ is

$R_2$ and $R_3$ are each independently lower alkyl, preferably methyl;

$R_4$ and $R_5$ are each independently $NO_2$, $N(R_6)_3{}^+$, CN, $COOR_7$, $SO_3H$ or $COR_8$, preferably $NO_2$;

$R_6$, $R_7$ and $R_8$ are each independently hydrogen or lower alkyl, preferably hydrogen or methyl, W is H or $CH=CH_2$, X and Y are each independently $OR_9$ or $NR_{10}R_{11}$, preferably X and Y are the same and most preferably X and Y are each $OR_9$, or X and Y together with the P to which they are attached form a 5- or 6-membered ring having the formula:

$R_9$, $R_{10}$, $R_{11}$ and $R_{12}$ are each independently hydrogen or lower alkyl, $R_9$ is preferably methyl, $R_{10}$, $R_{11}$ and $R_{12}$ are preferably hydrogen or methyl,

Z is O or NH, n is 1 to 20, preferably 1 to 8 when W is H, and 1 to 3 when W is $CH=CH_2$, and m is 1 or 2, said compound being an R or an S enantiomer or a mixture of R and S enantiomers.

In an embodiment of the subject invention, the above chiral selector is employed in a process of separating enantiomers of a β-amino alcohol compound which comprises contacting a mixture of enantiomers of a first compound having a first and a second optical configuration and having the formula:

wherein $R_{13}$ is aryl or a nitrogen, sulfur or oxygen containing heterocyclic ring, either of which may be unsubstituted or substituted with lower alkyl, lower alkoxyalkyl or lower alkenyloxy, $R_{14}$ is O, S or NH, $R_{15}$, $R_{16}$ and $R_{17}$ are each independently hydrogen or lower alkyl, and r, s and t are independently 0 or 1 with the chiral selector described above, said selector being an R or S enantiomer, under conditions effective to form a complex between an enantiomer of said first compound having said first optical configuration and the enantiomer of the chiral selector and recovering the non-complexed enantiomer of said first compound having said second optical configuration.

DESCRIPTION OF THE PREFERRED EMBODIMENTS

The present invention relates to the separation of β-amino alcohol compounds, particularly compounds known as β-blockers, by employing what is known as a chiral selector compound which can achieve separation of enantiomers without requiring derivatization of the enantiomers before effecting separation.

The process of the invention concerns a separation of enantiomers of underivatized amino alcohol compounds. This class of compounds may be identified by the general wherein wherein $R_{13}$ is aryl or a nitrogen, sulfur or oxygen containing heterocyclic ring, either of which may be unsubstituted or substituted with lower alkyl, lower alkoxyalkyl or lower alkenyloxy, $R_{14}$ is O, S or NH, $R_{15}$, $R_{16}$ and $R_{17}$ are each independently hydrogen or lower alkyl, and r, s and t are independently 0 or 1.

These compounds are of the R or S optical configuration and when prepared are usually produced as the racemic modification. Hence, the necessity for achieving separation.

Among the preferred β-amino alcohol compounds, which may be separated by the process of the subject invention, are pharmaceutical compounds known as β-blockers. In one group of β-blockers as depicted by the general formula, $R_{14}$ is O, and r is 1, while in another similar group as depicted by the general formula, r is O, thereby eliminating $R_{14}$ from the formula. The structures of commonly employed β-blockers are depicted in Table I, below:

TABLE I

β-Blocker structures

Metoprolol

TABLE I-continued

β-Blocker structures

Oxprenolol

Propanolol

Pronethalol

Pindolol

Bufuralol

The substituents in the formulas herein are described as follows:

As employed herein, the lower alkyl groups, singly or in combination with other groups, contain up to 6 carbon atoms which may be in the normal or branched configuration including methyl, ethyl, propyl, isopropyl, butyl, isobutyl, t-butyl, amyl, pentyl, hexyl and the like. The preferred alkyl groups contain 1 to 3 carbon atoms.

The lower alkoxyalkyl groups, singly or in combination with other groups, contain up to 12 carbon atoms with each alkoxy or alkyl group containing up to 6 carbon atoms which may be in the normal or branched configuration including for example, methoxymethyl, methoxyethyl, methoxypropyl, methoxyhexyl, ethoxymethyl, ethoxypropyl, propoxymethyl, propoxyhexyl, butoxyethyl, butoxypentyl, pentoxyethyl, pentoxyhexyl, hexoxyethyl, hexoxybutyl and the like. the preferred alkoxy and the preferred alkyl groups each contain 1 to 3 carbon atoms.

The lower alkenyloxy groups, singly or in combination with other groups contain up to 6 carbon atoms which may be in the normal or branched configuration including, for example, ethenyloxy, propenyloxy, butenyloxy, pentenyloxy and hexenyloxy and the like. The preferred alkenyloxy groups contain 2 to 3 carbon atoms.

The aryl groups are aromatic rings containing from 6 to 10 ring carbon atoms. The aryl groups include phenyl, β-naphthyl and β-naphthyl. The aryl group is preferably phenyl.

As employed herein, the expression "nitrogen, sulfur or oxygen containing heterocyclic ring" is meant to include those heterocyclic rings which include at least one sulfur, nitrogen or oxygen ring atom but which may include one or several of said atoms. The expression also includes saturated, and unsaturated heterocyclics as well as the heteroaromatic rings. These groups contain from 5 to 10 ring atoms on the heterocyclic moiety. Representative heterocyclics include furan, thiphene, pyrrole, pyridine, pyrazole, pyrazine, pyrimidine, pyridazine, oxazole, quinoline, isoquinoline, indole, benzothiophene, benzofuran, imidazole, benzoxazole, piperazine, tetrahydrofuran and the like. The preferred heterocyclics are indolyl, benzothienyl and benzofuranyl, especially 2- or 5-indolyl, 2- or 5-benzothienyl and 2- or 5-benzofuranyl.

The chemical compound employed as the chiral selector is depicted in the following formula:

wherein $R_1$ is preferably $R_1$ is

$R_2$ and $R_3$ are each independently lower alkyl, preferably methyl;

$R_4$ and $R_5$ are each independently $NO_2$, $N(R_6)_3^+$, $CN$, $COOR_7$, $SO_3H$ or $COR_8$, preferably $NO_2$;

$R_6$, $R_7$ and $R_8$ are each independently hydrogen or lower alkyl, preferably hydrogen or methyl, W is H or $CH=CH_2$, X and Y are each independently $OR_3$ or $NR_{10}R_{11}$, preferably X and Y are the same and most preferably X and Y are each $OR_9$, or X and Y together with the P to which they are attached form a 5- or 6-membered ring having the formula:

$R_9$, $R_{10}$, $R_{11}$ and $R_{12}$ are each independently hydrogen or lower alkyl, $R_9$ is preferably methyl, $R_{10}$, $R_{11}$ and $R_{12}$ are preferably hydrogen or methyl,

Z is O or NH, n is 1 to 20, preferably 1 to 8 when W is H, and 1 to 3 when W is CH=CH$_2$, and m is 1 or 2, said compound being an R or an S enantiomer or a mixture of R and S enantiomers.

The preferred chiral selector for effecting separation of β-amino alcohol compounds, particularly the β-blockers, is the chemical compound having the formula:

hereinafter identified as CS-6 and also known by its name, dimethyl N-(3,5-dinitrobenzoyl)-α-amino-2,2-dimethyl-4-pentenyl phosphonate.

The chiral selectors of the invention may be prepared by conventional chemical preparative techniques. For illustrative purposes the preparation of the preferred chiral selector is described below, but one skilled in the art can readily appreciate the modifications necessary to prepare other chiral selectors within the scope of the chemical formula employed herein to depict the useful chiral selectors.

The synthetic sequence used to prepare CS-6 is shown in Table II below.

lyl imine which adds dimethyl phosphite to give, after workup, the α-amino phosphonate. The crude α-amino phosphonate is acylated with 3,5-dinitrobenzoyl chloride to afford the racemic precursor of CS-6, resolvable on a variety of known n-basic chiral stationary phases (CSPs). Preparative resolution of CS-6 can be accomplished using a large column containing a N-2-(naphthyl)alanine-based CSP. The enantiomerically pure phosphonate can be covalently bonded to 3-mercaptopropyl-silanized silica using 2-2'-azobis(2-methylpropionitrile) as an initiator. The modified silica gel is slurry packed into a 120×4.6 mm stainless steel column, endcapped with hexamethyldisilizane, and can then be evaluated for its ability to separate the enantiomers of an assortment of β-blockers and β-blocker analogs.

Enantiomer separation by means of the chiral selectors of the invention may be achieved in a variety of techniques known in the art. In one embodiment the chiral selector may form the active portion of the stationary phase in a HPLC column as described above. Since the chiral selectors of the invention are optically active, it is necessary to separate the chiral selector so that either the R or the S enantiomer of the chiral selector is employed as part of the stationary phase in the column depending upon which of the enantiomers to be separated is to be preferentially bound to the chiral selector. In this embodiment the terminal W of the formula must be CH=CH$_2$ so as to permit the chiral selector to be immobilized on a support which is suitable for use in chromatographic applications. In one configuration the chiral selector is immobilized by covalently bonding it to silanized silica.

The effect of temperature on the chromatographic behavior of β-blocker enantiomers is unusual. The reduction of temperature is found to reduce the retention of the least retained enantiomer when employing the chiral selectors of the invention, while increasing the retention of the more retained enantiomer without appreciable band broadening.

The techniques of enantiomer separation by HPLC are known in the art. Commercially available HPLC

TABLE II

This preparation begins with an aldehyde, 4-pentena-1,2,2-dimethyl, readily available from the reaction of allyl alcohol and isobutyraldehyde. This aldehyde has a terminal double bond, which serves as a means for attachment to silica to form a CSP in a HPLC column, and is nonenolizable. Treatment of the aldehyde with sodium hexamethyldisilamide affords the N-trimethylsicolumns employing chiral stationary phases, such as those available from Regis Chemical Company can be employed in practicing the subject invention. See, for example, "Systematic Studies of Chiral Recognition Mechanisms," W. H. Pirkle, et al., Pages 23-35 in "Chiral Separations," Stephenson and Wilson, ed., Plenum Press, New York, 1988, the contents of which are incorporated herein by reference).

In another embodiment, the chiral selectors of the subject invention may be employed to effect separations employing semi-permeable membranes wherein the chiral selector forms part of a mobile phase. Such techniques are also well known employing semi-permeable membranes including those in the form of hollow fiber membranes. In this embodiment, it is preferred that the terminal W in the formula of the chiral selector should be hydrogen to minimize covalent bonding by the chiral selector. In one particularly useful embodiment, the chiral selector forms part of a liquid membrane passing on one side of a semi-permeable barrier with the enantiomers to be separated passing on the other side of the barrier. The pores of the barrier become impregnated with the liquid membrane containing the chiral selector. One of the enantiomers complexes with the chiral selector, passes through the barrier into the moving liquid membrane and is conducted to a second location where disassociation takes place. This technique is disclosed in commonly assigned patent application Ser. No. 528,007, filed May 23, 1990, now U.S. Pat. No. 5,080,795 the contents of which are incorporated herein by reference.

EXAMPLES

Apparatus

Chromatography was performed using either of two systems: system one consists of an Anspec-Bischoff model 2200 isocratic HPLC pump, a Beckman 210 injector with 20 $\mu$L sample loop, a Milton Roy LDC uv Monitor D ® fixed wavelength detector operating at 254 nm, and a Kipp and Zonen BD 41 Dual channel recorder. A Rudolph Autopol III with a 20-cm flow cell was used to monitor the sign of $[\alpha]_D$. System two consists of an Anspec-Bischoff model 2200 isocratic HPLC pump, a Rheodyne 7125 injector with 20 $\mu$L sample loop, two Milton Roy LDC uv Monitor D ® fixed wavelength detectors connected in series operating at 254 nm and 280 nm and a Kipp and Zonen BD 41 Dual channel recorder.

The allyl alcohol, isobutyraldehyde and dimethyl phosphite were purchased from Aldrich Chemical Company and distilled prior to use. The 2-acetylbenzofuran was used as received from Aldrich Chemical Company. DNB PG is available from Regis Chemical Company as is the N-(2-naphthyl)alanine undecyl ester CSP.

Preparation of Dimethyl N-(3,5-dinitrobenzoyl)-α-amino-2,2-dimethyl-4-pentenyl phosphonate (CS-6) (See Table II, infra.)

A 100 ml oven dried flask was charged with 2.20 g (12 mmol) of sodium hexamethyldisilamide and 50 ml of dry THF followed by 1.75 g (12 mmol) of aldehyde, 4-pentenal, 2,2-dimethyl, and magnetically stirred under a $N_2$ atmosphere at room temperature. After 1 hour, dimethyl phosphite 2.50 g (22.7 mmol) was added and the cloudy mixture brought to reflux for 24 hours. After cooling, the reaction mixture was diluted with 200 ml of $Et_2O$, followed by 100 ml of saturated $NaHCO_3$, the resulting mixture was stirred for 1 hour, the phases were separated and the organic layer was washed with 50 ml $H_2O$ then 50 ml of saturated NaCl. The combined aqueous layers were back extracted with three 50 ml portions of $CH_2Cl_2$. The combined organic layers were dried over $Na_2CO_3$. After filtration, the solution of crude amino phosphonate was treated with 3.51 g (15 mmol) of 3,5-dinitrobenzoyl chloride and 100 ml of 1:1 $H_2O$ and saturated $NaHCO_3$. After stirring for one hour, the aqueous layer was removed and replaced with 100 ml of 1:1 $H_2O$ and saturated $NaHCO_3$. After stirring for an additional hour, the layers were separated and the organic layer was washed with 50 ml of saturated NaCl, dried over $MgSO_4$ and concentrated under reduced pressure. After column chromatography on silica using 2:1 $CH_2Cl_2:Et_2O$ as eluent, ($\pm$) CS-6 was obtained as a colorless oil (1.35 g 25% yield). TLC $R_f=0.30$ (Silica/1:1 $CH_2Cl_2:Et_2O$). $^1H$ NMR ($C^2HCl_3$) $\delta$ 1.15 two s 6H; 2.24 m 1H; 2.32 m 1H; 3.75 d (J=16 Hz) 3H; 3.80 d (J=16 Hz) 3H; 4.6–4.92 dd J=20, 10 Hz) 1H; 5.20 m 2H; 5.90 m 1H;7.4 d (J=10 Hz) 1H; 9.02 m 2H; 9.19 m 1H. $^{31}P\{_1H\}$ NMR ($C^2HCl_3$) $\delta$25.78 (ref 85% $H_3PO_4$). IR (KBr, neat) 3248, 3098, 2961, 1734, 1670, 1630, 1541, 1344, 1284, 1234, 1035 cm$^{-1}$. mass spectrum (70 eV) 415 (0.8); 238 (18.0); 195 (100); 149 (82.5); 75 (76.7). high resolution mass spectrum, calculated for $C_{16}H_{22}N_3O_8P$: 415.1144. Found: 415.1137.

Resolution of Racemic CS-6

Enantiomer separation was accomplished by medium pressure liquid chromatography on a 1×30 in. column packed with (+)-(R)-N-(2-naphthyl)-alanine undecyl ester CSP bonded to 60 um irregular silica. The mobil phase was 2% isopropyl alcohol in hexane. Two chromatographic fractions were collected. The first was (+)-(R)-CS-6 of 98% enantiomeric purity, as judged by HPLC assay on a Regis (R)-N-(2-naphthyl)-alanine column. The subsequently collected (−)-(S)-CS-6 was found to be of 99% enantiomeric purity. Each enantiomer was obtained as a colorless foam after drying in vacuo. The NMR spectrum of each enantiomer was identical to that of the racemate.

Chiral Stationary Phase of CS-6

Mercaptopropyl silica, 2.75 g, 0.60 g of enantiomerically pure (R)-CS-6 and 0.10 g of 2,2'-azobis(2-methylpropionitrile) were slurried in 30 mL of $CHCl_3$ and brought to reflux. After 36 h, the light red mixture was cooled and the derivatized silica was collected by filtration. The silica was washed sequentially with 100 mL of methanol, 50 mL of ethyl acetate, and 50 mL of diethyl ether. The modified silica was packed as a methanol slurry into a 120×4.6 mm I.D. column using conventional methods. Found: C, 5.80%; H, 1.03%; N, 0.69%. Calculated: 0.15 mmol/g (based on C); 0.16 mmol/g (based on N).

Analytes and Their Separation

The $\beta$-blockers samples were provided by pharmaceutical companies. Pindolol from Sandoz, Ltd., Basle, Switzerland. Metoprolol from Ayerst Laboratories, Inc. Proenthalol and Propranolol from Imperial Chemical Industries. Oxprenolol from Ciba-Giegy. Bufuralol and its methylated analogs were provided by Roche Products Limited.

Figure 1:
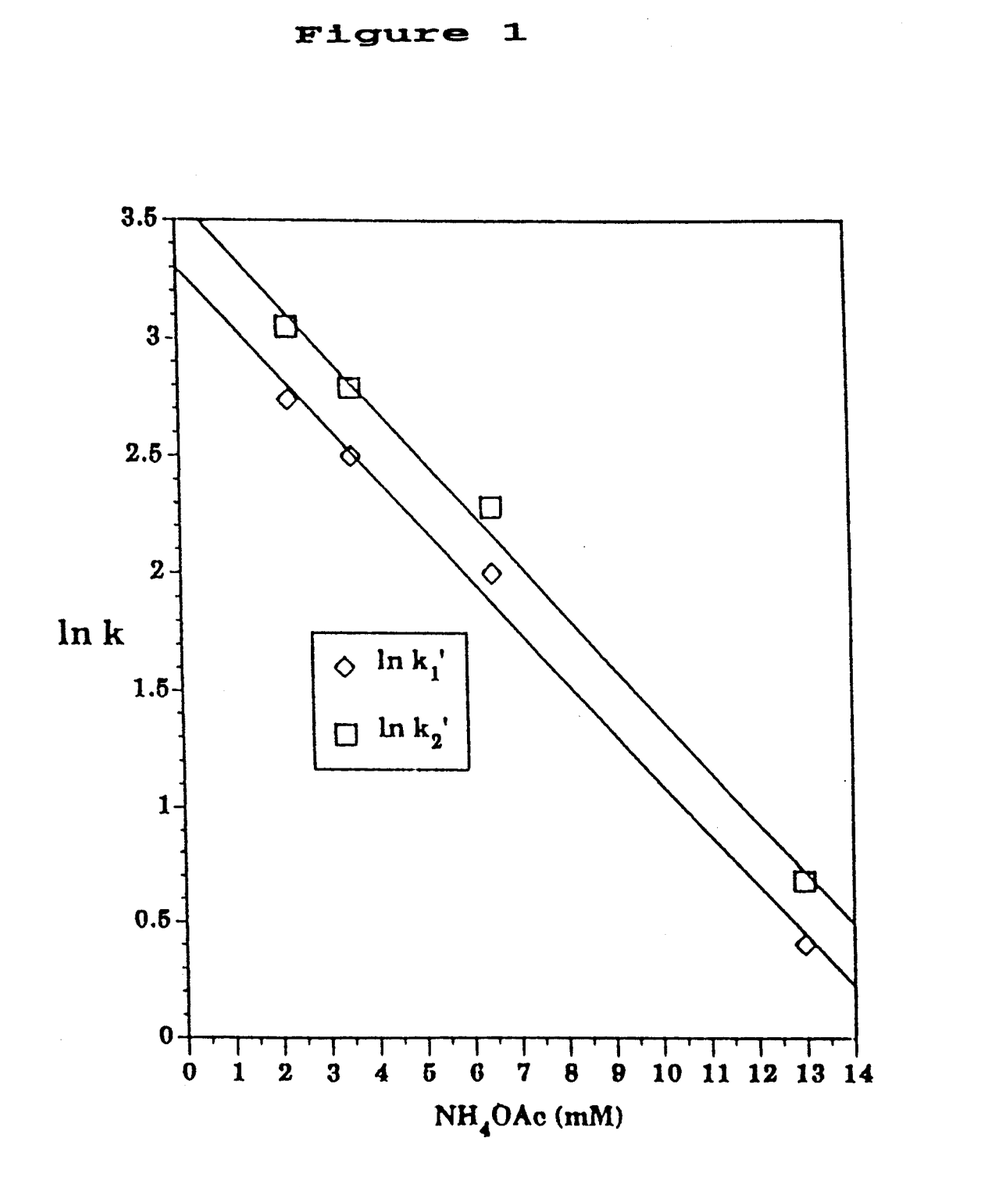
FIG. 1 is a graph of the relationship between the retention of enantiomers on a preferred chiral selector of the invention and the quantity of ammonium acetate in the mobile phase in an LC column.

Since the presence of a basic amino group in an analyte typically leads to long retention and peak tailing on silica-based $\pi$-acidic CSPs, control of mobile phase pH and/or addition of amines to the mobile phase are frequently used cures for such peak tailing. Mobile phases consisting of halocarbons and lower molecular weight molecular alcohols and containing a low concentration of ammonium acetate have permitted separation of enantiomers of propranolol on known CSPs. The ammonium acetate provides a means of protonating amino group of the β-blockers and reduces peak tailing. Increasing the concentration of the ammonium acetate in the mobile phase diminished retention of propanolol on CS-6, but did not drastically alter enantioselectivity, thus suggesting that the ammonium acetate competes with the protonated β-blockers for absorption sites. This behavior is shown in FIG. 1 using a chloroform-methanol mobile phase. In the case of preparative separations, the volatility of the mobile phase components including ammonium acetate makes it possible to retrieve the β-blocker simply by evaporation of the mobile phase under vacuum.

Enantiomeric mixtures of the β-blockers of interest and some of their analogs were subjected to separation with HPLC columns to compare the effectiveness of prior art chiral separators and CS-6 of the invention when forming the active part of the stationary phase in the column.

A mobile phase of 19:1 dichloromethane-ethanol containing 0.5 g/L (6.5 mM) of ammonium acetate was used. To improve reproducibility, a stock solution of ammonium acetate in absolute ethanol was prepared and diluted with dichloromethane as required. Comparative chromatographic data for six β-blockers were obtained using (R)-CS-6 of the invention and two known CSPs, a commercial covalent (R)-N-(3,5-dnitrobenzoyl)-phenylglycine derived phase (DNB PG), and (R)-dimethyl N-(3,5-dinitrobenzoyl)-α-amino-4-(3-propenyl-1-oxy) benzyl phosphonate (CPS-5). The results are presented in Table III.

TABLE III

Separation of the Enantiomers of Some β-Blockers

| Analyte | (R) DNB PG | | | (R) CSP 5 | | | (R) CSP 6 | | |
|---|---|---|---|---|---|---|---|---|---|
| | $\alpha^a$ | $k_1'^b$ | $[\alpha]_D^c$ | $\alpha^a$ | $k_1'^b$ | $[\alpha]_D^c$ | $\alpha^a$ | $k_1'^b$ | $[\alpha]_D^c$ |
| metoprolol | 1.05 | 9.86 | | 1.15 | 6.57 | | 1.16 | 2.57 | |
| oxprenolol | 1.00 | 16.10 | | 1.00 | 6.14 | | 1.00 | 2.28 | |
| pronethalol | 1.03 | 11.20 | | 1.06 | 12.36 | | 1.13 | 5.14 | |
| propranolol | 1.00 | 12.80 | | 1.34 | 13.40 | (+)R | 1.39 | 4.36 | (+)R |
| pindolol | 1.12 | 45.10 | | 1.12 | 51.10 | | 1.30 | 15.00 | |
| bufuralol | 1.16 | 4.94 | (+)R | 1.22 | 6.67 | (+)R | 1.93 | 2.79 | (+)R |

$^a$Chromatographic separation factor
$^b$The capacity factor for the first eluted enantiomer using 19:1 $CH_2Cl_2$:$CH_3CH_2OH$ with 0.5 grams/liter $NH_4O_2CCH_3$ as the mobile phase, flow rate of 2 mL per minute. The detector was operating at 254 nm.
$^c$Sign of $[\alpha]_D$ of the more strongly retained enantiomer as determined by a polarimetric HPLC detector. The letter refers to the absolute configuration of the more strongly retained enantiomer.

From these data, it is evident that the more π-basic β-blockers are the more strongly retained. However, enantio-selectivity does not necessarily parallel retention. Note that bufuralol is one of the more weakly retained, judged by $k_1'$, of the 8-blockers on CS-6, yet affords the largest separation factor in the table.

Figure 2A:
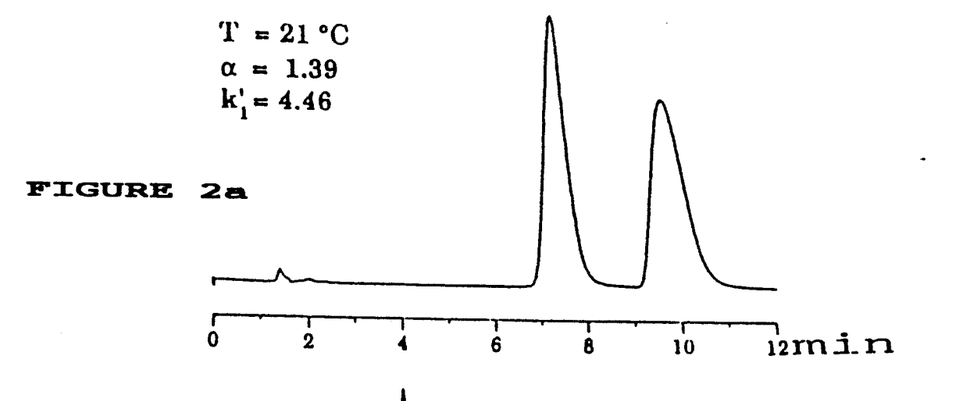
FIGS. 2A, 2B, 2C are a series of plots showing the effect of temperature at 21°, 0° and 24° C. and enantioselectivity on a preferred chiral selector of the invention.
Figure 2B:
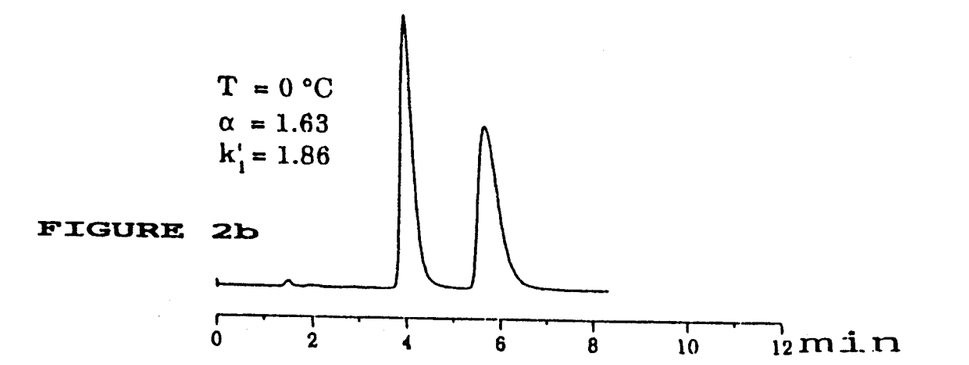
Figure 2C:
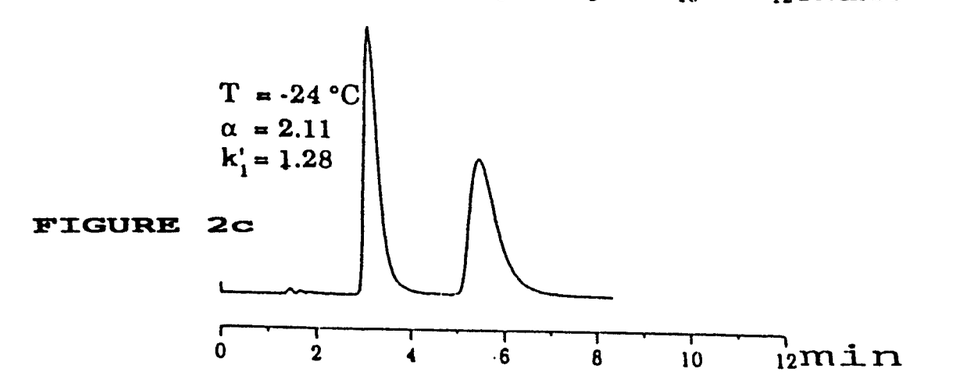
Figure 3A:
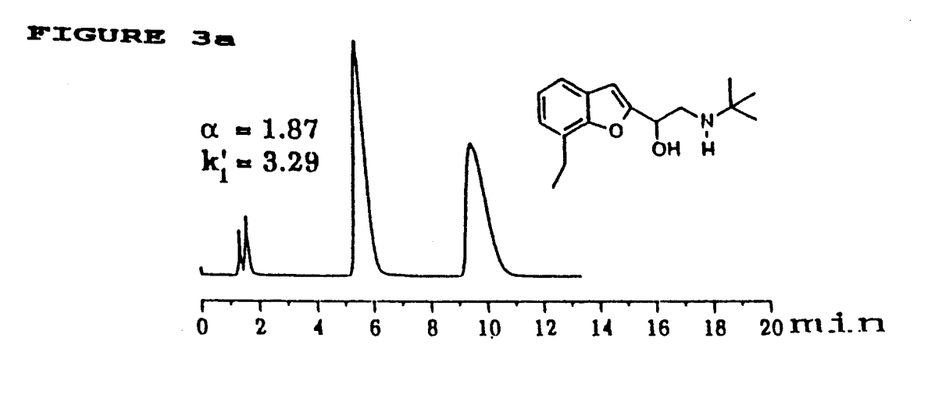
FIG. 3A, 3B and 3C are a series of plots is a plot showing the influence on ring methylation on the retention and enantioselectivity on several analogs of a preferred chiral selector.
Figure 3B:
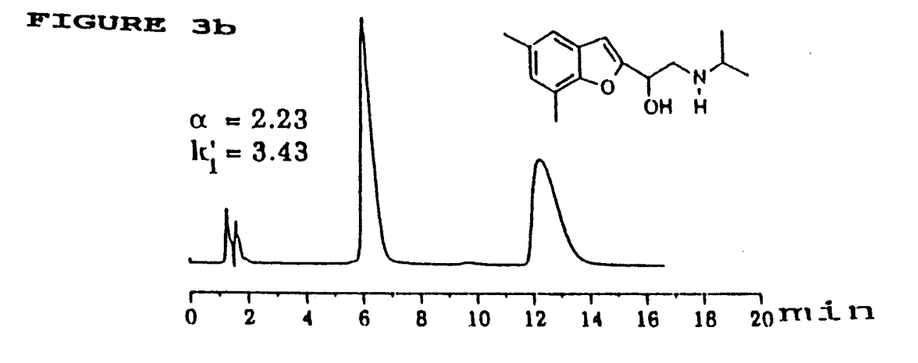
Figure 3C:
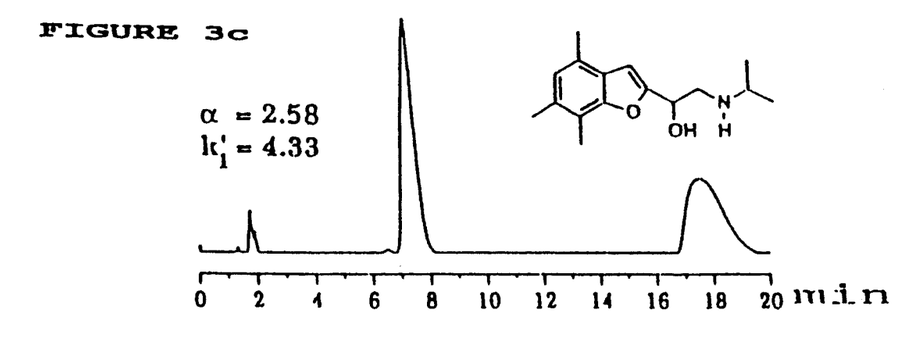

The elution orders on CSP-5 and CS-6 can be explained although this may not be in accord with the elution order noted on (R)-DNB PG. Owing to the Cahn-Ingold-Prelog priority sequence, (R)-CSP-5 and (R)-CS-6 are stereochemically equivalent to (S)-DNB PG. To further evaluate the chiral recognition process, the effect of temperature on β-blocker retention by CSP-5 and CS-6 was investigated. A linear van't Hoff response (i.e., a linear ln k' versus 1/T plot) is generally expected with increases in retention, enantioselectivity and peak width as the column temperature is reduced. Using the CSP-mobile phase combination described, nonlinear van't Hoff behavior was observed for an extended series of β-blockers and their analogs. As can be seen from the data in Table IV, there are dramatic increases in enantioselectivity with comparatively little accompanying peak broadening (see FIG. 2). In view of the number of equilibria possible in these rather complex systems, equilibria which may respond differently to temperature change, no rationalization of these observations can be offered.

TABLE IV

The Effect of Temperature Upon Retention and Enantioselectivity for Some of β-Blockers and Analogs using CS 6

| Analyte | 21° C. | | 0° C. | | −24° C. | |
|---|---|---|---|---|---|---|
| | $\alpha^a$ | $k_1'^b$ | $\alpha^a$ | $k_1'^b$ | $\alpha^a$ | $k_1'^b$ |
| metoprolol | 1.16 | 2.57 | 1.21 | 1.05 | 1.48 | 0.64 |
| oxprenolol | 1.00 | 2.28 | 1.00 | 0.75 | 1.03 | 0.50 |
| pronethalol | 1.13 | 5.14 | 1.21 | 2.21 | 1.31 | 1.50 |
| propranolol | 1.39 | 4.46 | 1.63 | 1.86 | 2.11 | 1.28 |
| pindolol | 1.30 | 15.0 | 1.43 | 7.29 | 1.72 | 6.71 |
| bufuralol | 1.93 | 2.79 | 2.50 | 1.43 | 4.08 | 0.73 |
| | 2.15 | 3.43 | 2.83 | 2.07 | 4.18 | 1.57 |
| | 2.23 | 3.28 | 3.04 | 1.86 | 4.44 | 1.46 |

TABLE IV-continued

The Effect of Temperature Upon
Retention and Enantioselectivity for
Some of β-Blockers and Analogs using CS 6

| Analyte | 21° C. $\alpha^a$ | 21° C. $k_1^{,b}$ | 0° C. $\alpha^a$ | 0° C. $k_1^{,b}$ | −24° C. $\alpha^a$ | −24° C. $k_1^{,b}$ |
|---|---|---|---|---|---|---|
|  | 2.58 | 4.43 | 3.44 | 2.57 | 5.03 | 2.21 |
|  | 1.75 | 4.14 | 2.38 | 1.86 | 3.76 | 1.13 |
|  | 1.64 | 4.01 | 2.08 | 1.80 | 3.08 | 1.08 |
|  | 1.63 | 1.71 | 1.94 | 1.19 | 3.02 | 0.73 |

[a]Chromatographic separation factor
[b]The capacity factor for the first eluted enantiometer using 19:1 CH$_2$Cl$_2$:CH$_3$CH$_2$OH with 0.5 grams/liter NH$_4$O$_2$CCH$_3$ as the mobile phase, flow rate of 2 mL per minute. The detector was operating at 254 nm.

Figure 4:
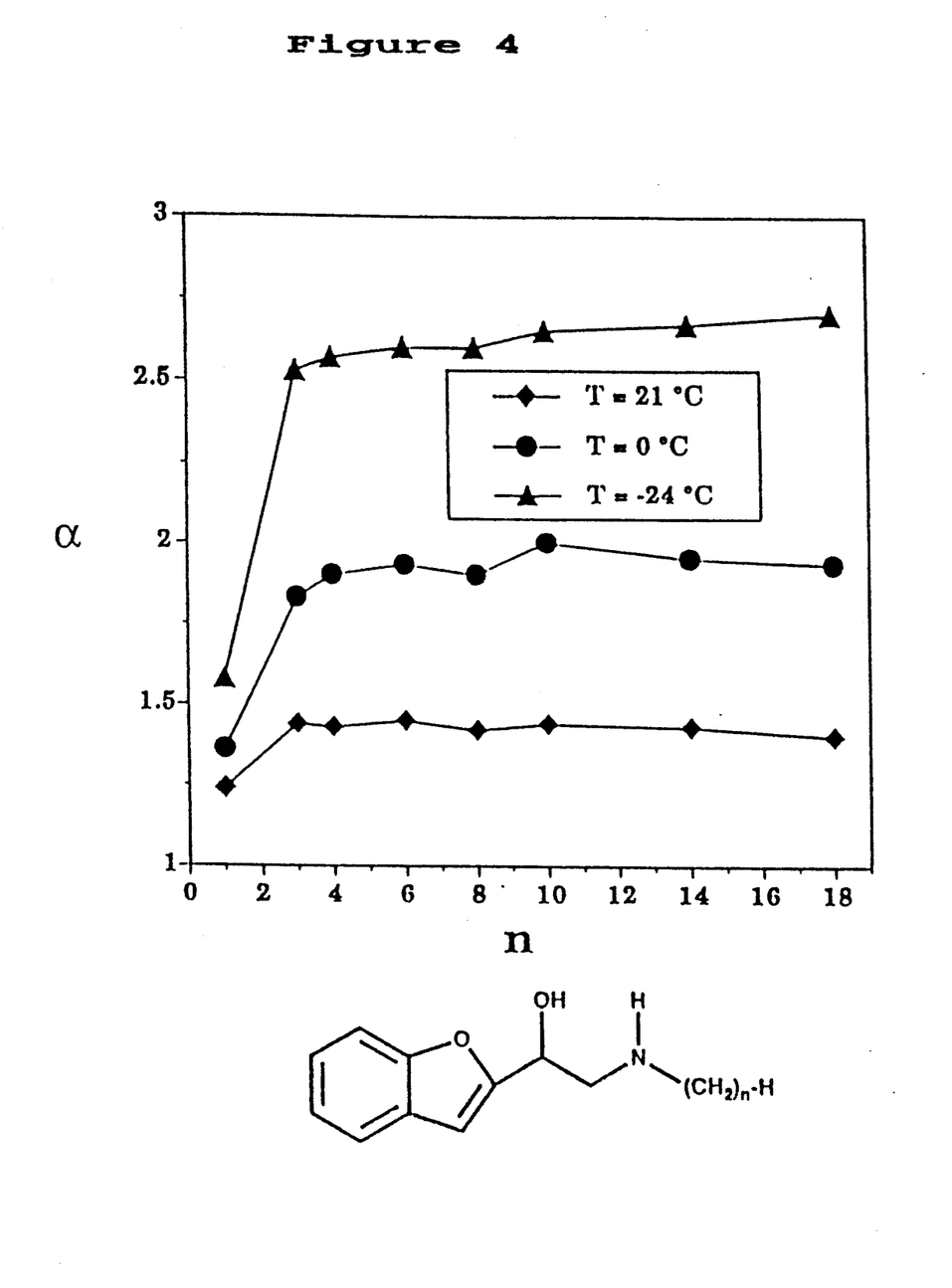
FIG. 4 is a graph showing the relationship between enantioselectivity on a preferred chiral selector of the invention and the number of methylenes in the N-alkyl substituent on a particular β-amino alcohol compound at three temperatures.

It was not surprising that the enantiomers of bufuralol were better resolved than those of propranolol. Unlike the latter two, bufuralol lacks the methylene group between the π-basic aromatic group and the stereogenic center. Consequently, it is more restricted conformationally, a circumstance often associated with appreciable degrees of enantioselectivity. Note that replacing the 7-ethyl substituent of bufuralol with two, or better, three, methyl substituents on the benzofuran ring enhances enantioselectivity by increasing the π-basicity without adding polar sites for additional bonding interactions with the stationary phase (see FIG. 3) which increase retention but may possibly reduce enantioselectivity. The methyl substituents enhance enantioselectivity relative to bufuralol even though the analogs have N-isopropyl substituents, shown herein to be inferior to N-t-butyl substituents in engendering enantioselectivity in bufuralol-like systems. For example, a series of bufuralol-like racemates was prepared by a synthetic route which allows variation of the N-alkyl substituent (see Table V, below). This sequence, similar to that reported for bufuralol, entails α-bromination of 2-acetylbenzofuran, reduction of the bromo ketone to the bromo alcohol with sodium borohydride, and the substitution of the desired n-alkylamine for the bromine. FIG. 4 shows the effect of the length of the N-alkyl substituent upon α at 21° C., 0° C., and −24° C. As may be seen, alkyl groups longer than propyl have negligible effect upon the magnitude of α, suggesting that the enantiomers show either no or little differential intercalation of the N-alkyl groups between strands of bonded phase.

TABLE V

Figure 5:
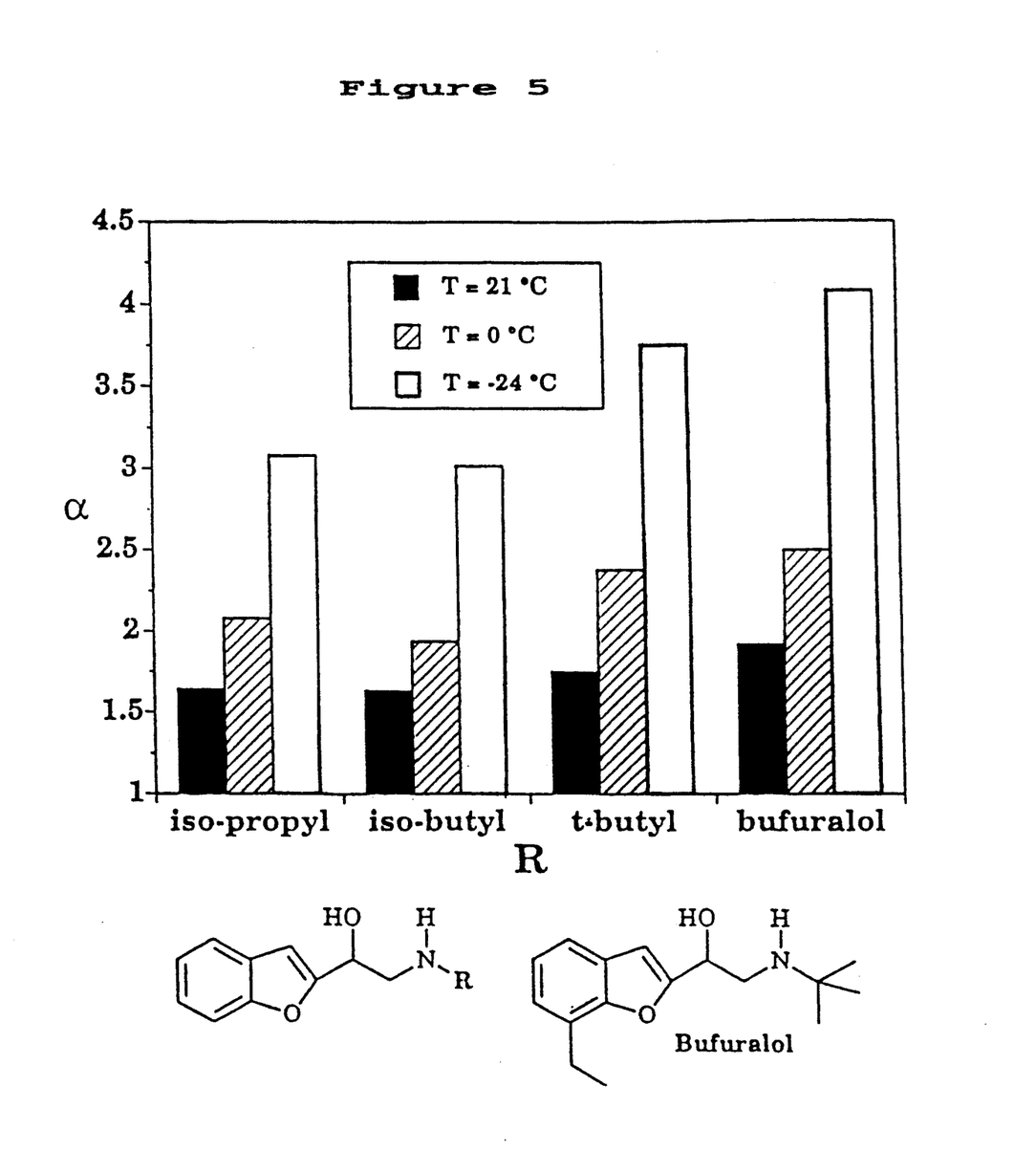
FIG. 5 is a graph showing the relationships between enantioselectivity on a preferred chiral selector of the invention and the alkyl substituent on the nitrogen of a particular β-amino alcohol compound at three temperatures.

In all instances, α increases dramatically as the temperature is diminished. Chromatographic response to temperature change of the bufuralol analogs having N-isopropyl, N-isobutyl and N-t-butyl substituents is shown in Table IV. The N-isopropyl and N-isobutyl analogs show comparable levels of enantioselecitvity at ambient temperature and are exceeded in this respect by the N-t-butyl analog. This difference is accentuated at lower temperatures. All three analogs show lower selectivities than bufuralol, doubtless owing to the absence of a π-basicity-enhancing alkyl substituent on the benzofuran system. FIG. 5 shows this relationship between α and the alkyl group on the nitrogen of bufuralol analogs at three temperatures when CS-6 is the chiral selector.

Elution orders were rigorously established using β-blocker samples of known absolute configuration. In some instances, the signs of the rotation of the enantiomers were related to elution orders using a polarimetric detector in orders on CSP-5 and CS-6 are consistent with the a prior formulated chiral recognition model, such as that of Table VI below, as are the structure-activity relationships noted. It is evident that the chiral selectors of the invention, particularly CS-6 are useful for both analytical and preparative scale separations of a variety of β-blockers, no derivatization being required.

TABLE VI
Chiral Recognition model

What is claimed is:

1. A chemical compound having the formula:

wherein

$R_1$ is $R_2$ and $R_3$ are each independently lower alkyl,
$R_4$ and $R_5$ are each independently $NO_2$, $N(R_6)_3^+$, $CN$, $COOR_7$, $SO_3H$ or $COR_8$,
$R_6$, $R_7$ and $R_8$ are each independently hydrogen or lower alkyl,
W is H or $CH=CH_2$,
X and Y are each independently $OR_9$ or $NR_{10}R_{11}$, or X and Y together with the P to which they are attached form a 5- or 6-membered ring having the formula:

$R_9$, $R_{10}$, $R_{11}$ and $R_{12}$ are each independently hydrogen or lower alkyl,
Z is O or NH,
n is 1 to 8 when W is H, or 1 to 3 when W is $CH=CH_2$, and
m is 1 or 2, said compound being an R or an S enantiomer or a mixture of R and S enantiomers.

2. The compound of claim 1 wherein $R_1$ is  and $R_2$ and $R_3$ are each methyl,
n is 1 or 2,
X and Y are each $OR_9$, and
$R_9$ is hydrogen or methyl.

3. The compound of claim 2 wherein
W is $CH=CH_2$,
n is 1,
$R_4$ and $R_5$ are each $NO_2$, and
$R_9$ is methyl.

4. The compound of claim 2 wherein
W is hydrogen,
$R_4$ and $R_5$ are each $NO_2$, and
$R_9$ is methyl.

5. A process of separating enantiomers which comprises contacting a mixture of enantiomers of a first compound having a first and a second optical configuration and having the formula:

$$R_{13} \overset{(R_{14})_r}{\frown} (H_2C)_s \overset{OH}{\frown} \overset{H}{\underset{(CH_2)_t}{N}} CR_{15}R_{16}R_{17}$$

wherein
$R_{13}$ is aryl or a nitrogen, sulfur or oxygen containing heterocyclic ring, either of which may be unsubstituted or substituted with lower alkyl, lower alkoxyalkyl or lower alkenyloxy,
$R_{14}$ is O, S or NH,
$R_{15}$, $R_{16}$ and $R_{17}$ are each independently hydrogen or lower alkyl, and
r, s and t are independently 0 or 1,
with a chiral selector, said selector being an R or S enantiomer of the compound of claim 1, under conditions effective to form a complex between an enantiomer of said first compound having said first optical configuration and an enantiomer of said compound of claim 1 and recovering the non-com- plexed enantiomer of said first compound having said second optical configuration.

6. A process according to claim 5 including the additional step of:
subjecting the complex to conditions effective to dissociate the enantiomer of said first compound having said first optical configuration from the enantiomer of said first compound of claim 1 and recovering the enantiomer of said first compound having said first optical configuration.

7. A process according to claim 5 wherein the stationary phase in an LC column comprises said chiral selector and the less retained enantiomer of said first compound having said second optical configuration elutes from said column prior to said first compound having said first optical configuration.

8. The process according to claim 5 wherein a liquid membrane comprising said chiral selector is passed in contact with one side of a semi-permeable membrane and said mixture of enantiomers of said first compound is in contact with the other side of said semi-permeable membrane.

9. A process according to claim 7 wherein

W is CH=CH$_2$,
n is 1,
X and Y are each OR$_9$, and
R$_9$ is hydrogen or methyl.

10. A process according to claim 8 wherein

W is H,
n is 1 or 2,
X and Y are each OR$_9$, and
R$_9$ is hydrogen or methyl.

11. A process according to claim 9 or 10 wherein
R$_2$ and R$_3$ are each methyl,
R$_4$ and R$_5$ are each NO$_2$, and
R$_9$ is methyl.

12. A process according to claim 11 wherein

R$_{14}$ is O;
r and s are each 1 and t is 0; and
R$_{15}$ is H and R$_{16}$ and R$_{17}$ are each CH$_3$.

13. A process according to claim 11 wherein

R$_{14}$ is O,
r and s are each 1 and t is 0; and
R$_{15}$ is H and R$_{16}$ and R$_{17}$ are each CH$_3$.

14. A process according to claim 11 wherein

R$_{14}$ is O;
r and s are each 1 and t is 0; and
R$_{15}$ is H and R$_{16}$ and R$_{17}$ are each CH$_3$.

15. A process according to claim 11 wherein

R$_{14}$ is O;
r and s are each 1 and t is 0; and
R$_{15}$ is H and R$_{16}$ and R$_{17}$ are each CH$_3$.

16. A process according to claim 11 wherein r, s and t are each 0; and
R$_{15}$ is H and R$_{16}$ and R$_{17}$ are each CH$_3$.

17. A process according to claim 11 wherein or r, s and t are each 0;
R$_{15}$ and R$_{16}$ are each independently H or CH$_3$; and
R$_{17}$ is CH$_3$ or 18. An LC column wherein the stationary phase comprises an R or an S enantiomer of the compound of claim 1 immobilized on a support effective for use in chromatographic separation.

19. An LC column wherein the stationary phase comprises an R or an S enantiomer of the compound of claim 3 immobilized on a support effective for use in chromatographic separation.

20. A method of producing a stationary phase for an LC column which comprises immobilizing an R or an S enantiomer of the compound of claim 1 on a support effective for use in chromatographic separation.

21. A method of producing a stationary phase for an LC column which comprises immobilizing an R or an S enantiomer of the compound of claim 3 on a support effective for use in chromatographic separation.

* * * * *

UNITED STATES PATENT AND TRADEMARK OFFICE
CERTIFICATE OF CORRECTION

PATENT NO. : 5,254,258
DATED : October 19, 1993
INVENTOR(S) : William H. Pirkle, et al.

It is certified that error appears in the above-indentified patent and that said Letters Patent is hereby corrected as shown below:

Title page, item [57],

In the Abstract, line 27: "$COOR_2$" should read --$COOR_7$--

In the Abstract, line 35: after "formula" insert --:--

Column 2, line 67: "[1" should read --(1--

Column 5, line 67: "FIG." should read --Figures--

Column 5, line 67: delete "is a plot"

Column 6, line 26: delete "wherein" and after "general" insert --formula:--

Column 8, line 8: " -naphthyl" should read -- $\alpha$-naphthyl--

Column 8, line 64: "$OR_3$" should read --$OR_9$--

Column 10, line 5: "n-basic" should read -- $\pi$-basic--

Column 12, line 54: "8-blockers" should read -- $\beta$-blockers--

UNITED STATES PATENT AND TRADEMARK OFFICE
CERTIFICATE OF CORRECTION

PATENT NO. : 5,254,258
DATED : October 19, 1993
INVENTOR(S) : William H. Pirkle, et al.

It is certified that error appears in the above-indentified patent and that said Letters Patent is hereby corrected as shown below:

Column 13, line 2: after "protonating" insert --the--

Column 13, lines 42-43: "dnitrobenzoyl" should read --dinitrobenzoyl--.

Column 14, line 11, Table III: "51.10" should read --50.10--

Column 14, line 21: "8-Blockers" should read --$\beta$-blockers--

Column 17, line 12: after "in" insert --series with the ultraviolet detectors. The observed elution--

Signed and Sealed this

Ninth Day of August, 1994

Attest:

BRUCE LEHMAN

Attesting Officer

Commissioner of Patents and Trademarks